(12) United States Patent
Verbeeck et al.

(10) Patent No.: US 10,477,887 B2
(45) Date of Patent: Nov. 19, 2019

(54) SMOKING MACHINE

(71) Applicant: PHILIP MORRIS PRODUCTS S.A., Neuchatel (CH)

(72) Inventors: Jan Verbeeck, Gurmels (CH); John Faulkner, Gorgier (CH)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 231 days.

(21) Appl. No.: 14/890,552

(22) PCT Filed: Jun. 23, 2014

(86) PCT No.: PCT/EP2014/063152
§ 371 (c)(1),
(2) Date: Nov. 11, 2015

(87) PCT Pub. No.: WO2014/206934
PCT Pub. Date: Dec. 31, 2014

(65) Prior Publication Data
US 2016/0113321 A1    Apr. 28, 2016

(30) Foreign Application Priority Data

Jun. 23, 2014  (EP) ..................................... 13173401

(51) Int. Cl.
*A24C 5/34* (2006.01)
*G01N 33/00* (2006.01)

(52) U.S. Cl.
CPC .............. *A24C 5/34* (2013.01); *A24C 5/3406* (2013.01); *G01N 33/0022* (2013.01); *G01N 33/0098* (2013.01)

(58) Field of Classification Search
CPC .... A24C 5/34; A24C 5/3406; G01N 33/0022; G01N 33/0098
See application file for complete search history.

(56) References Cited

U.S. PATENT DOCUMENTS 1,190,926 A    7/1916  Lotozky
3,732,874 A *  5/1973  Wagner ............... A24C 5/3406
                                                     131/182
(Continued)

FOREIGN PATENT DOCUMENTS

CH    503 986 A      2/1971
CN   201133882 Y    10/2008
(Continued)

OTHER PUBLICATIONS

International Search Report dated Nov. 19, 2014 in PCT/EP14/63152 Filed Jun. 23, 2014.
(Continued)

*Primary Examiner* — Marrit Eyassu
(74) *Attorney, Agent, or Firm* — Oblon, McClelland, Maier & Neustadt, L.L.P.

(57) ABSTRACT

A modular smoking system is provided, including a substantially annular carousel that includes a plurality of smoking article ports configured to receive smoking articles and a plurality of analysis ports, the carousel having an inner surface and an outer surface radially spaced from the inner surface, in which a plurality of identically-dimensioned aerosol-flow channels are defined through the carousel, each aerosol-flow channel extending radially through the carousel between a smoking article port located at the inner surface of the carousel and a corresponding analysis port located at the outer surface of the carousel, and at least one aerosol analysis module located radially outwards from the outer surface of the carousel and configured to couple to the analysis port for analysis of an aerosol generated by a smoking article coupled to a smoking article port.

14 Claims, 4 Drawing Sheets

(56) References Cited

U.S. PATENT DOCUMENTS

| | | | | |
|---|---|---|---|---|
| 3,994,307 | A | * 11/1976 | Loeffler | A24C 5/3406 |
| | | | | 131/330 |
| 4,140,003 | A | * 2/1979 | Pillsbury, Jr. | A24C 5/3406 |
| | | | | 73/23.31 |
| 4,721,060 | A | * 1/1988 | Cannon | A61D 7/04 |
| | | | | 119/420 |
| 4,858,628 | A | 8/1989 | Norman et al. | |
| 5,113,689 | A | * 5/1992 | Piade | A24C 5/3406 |
| | | | | 73/23.21 |
| 7,100,420 | B2 | * 9/2006 | Read | A24C 5/3406 |
| | | | | 131/330 |

FOREIGN PATENT DOCUMENTS

| | | | |
|---|---|---|---|
| CN | 102680648 A | 9/2012 | |
| DE | 41 23 098 A1 | 1/1993 | |
| EP | 2 193 727 A1 | 6/2010 | |
| GB | 1190925 | 5/1970 | |
| GB | 1190926 A * | 5/1970 | A24C 5/34 |
| JP | 2002-171954 | 6/2002 | |
| JP | 2002171954 A * | 6/2002 | |

OTHER PUBLICATIONS

Combined Chinese Office Action and Search Report dated Aug. 2, 2017 in Patent Application No. 201480031546.1(with English Translation).

Japanese Office Action dated May 28, 2018 in corresponding Japanese Application No. 2016-520524 with English translation, citing document AO therein, 12 pages.

* cited by examiner

SMOKING MACHINE

TECHNICAL FIELD

The present invention relates to a smoking machine, and more particularly to a multi-port smoking machine, and to a method of analysing aerosol generated by a plurality of smoking articles.

DESCRIPTION OF THE RELATED ART

Multi-port smoking machines for collecting and analysing the constituents of tobacco smoke produced by a plurality of cigarettes or other smoking articles under controlled smoking conditions are well known in the art. In use, the mouth end of the cigarettes are placed in holders connected to smoking ports on the machine, and air is drawn through the lit cigarettes at regular intervals using one or more mechanically driven gas syringes or pumps. Particulate and vapour phase constituents of the mainstream tobacco smoke drawn through the cigarettes are collected using one or more trapping systems, such as for example glass fibre (Cambridge) filters, impingers and gas collection bags, and then analysed to determine, for example, yields of tar, nicotine and carbon monoxide.

Two general types of multi-port smoking machines are known: linear smoking machines and rotary smoking machines.

In linear smoking machines, for example, the LM450 Linear Smoking Machine available from Borgwaldt KC in Hamburg. Germany, each smoking port is coupled to a separate syringe or pump, which draws air through a cigarette placed in a holder connected to that smoking port. In use, mainstream smoke is drawn simultaneously through each cigarette and collected separately, i.e. the mainstream smoke is collected individually per smoking port.

In rotary smoking machines, for example, the RM200A Rotary Smoking Machine available from Borgwaldt KC in Hamburg. Germany, the smoking ports are mounted on a head that is rotated relative to a single static syringe or pump, which draws air through cigarettes placed in holders connected to the smoking ports in turn. In use, the mainstream smoke drawn successively through each cigarette is collected cumulatively.

By allowing a cumulative mainstream smoke sample from a large number of smoking articles to be collected in a single run, rotary smoking machines advantageously generate a robust smoke matrix in a short period of time.

A number of smoking articles in which tobacco material is heated to form an aerosol that is inhaled by a consumer, rather than combusted to form smoke, have been proposed in the art. In one known type of heated smoking article, an aerosol is produced by the transfer of heat from a combustible fuel element or heat source to a physically separate tobacco material, which may be located within, around or downstream of the fuel element. In another, type of heated smoking article, tobacco material is heated by one or more electrical heating elements to produce an aerosol.

It would be desirable to provide a smoking machine that allows for the collection and analysis of smoke from different types of smoking article, and for different types of analysis to be carried out. It would further be desirable to provide a smoking machine that can operate in both a "linear" mode i.e. a mode in which aerosol is collected per smoking article, and in a "rotary" mode i.e. a mode in which aerosol can be collected cumulatively for a plurality of smoking articles and which an identical path length for aerosol between each smoking article and a trap or analyser.

SUMMARY

In a first aspect, there is provided a modular smoking system comprising: a carousel module comprising a substantially annular carousel, a plurality of smoking article ports for receiving smoking articles, and a plurality of analysis ports, the carousel having an inner surface and an outer surface radially spaced from the inner surface, in which a plurality of identically-dimensioned aerosol-flow channels are definable through the carousel, each aerosol-flow channel extending radially through the carousel between a smoking article port located at the inner surface of the carousel and an analysis port located at the outer surface of the carousel, and at least one aerosol analysis module located radially outwards from the outer surface of the carousel and couplable to an analysis port for analysis of an aerosol generated by a smoking article coupled to a smoking article port.

The modular smoking system offers the advantage that the aerosol analysis module can be formed as a separable module from the carousel module. This allows different analysis modules to be coupled to the analysis port and to be removed for maintenance and calibration. By providing an analysis port or ports on an outer surface of the carousel, the analysis module or modules can be readily accessed both during operation and during the set up of the system. And there is ample space for a plurality of analysis modules.

In this context the term "annular carousel" is not limited to a carousel having a circular cross-section but may be of any cross section, such as a regular polygonal cross-section.

A smoking article may be any article comprising an aerosol-forming substrate that is capable of releasing volatile compounds that can form an aerosol. The smoking article may be a non-combustible smoking article or may be a combustible smoking article. A non-combustible smoking article releases volatile compounds without the combustion of the aerosol-forming substrate, for example by heating the aerosol-forming substrate, or by a chemical reaction, or by mechanical stimulus of an aerosol-forming substrate. A combustible smoking article releases an aerosol by direct combustion of an aerosol-forming substrate, for example as in a conventional cigarette. In this context, an aerosol means a dispersion of solid particles or liquid droplets or a combination of solid particles and liquid droplets in a gas. An aerosol may be visible or invisible. An aerosol may include vapours of substances that are ordinarily liquid or solid at room temperature as well as solid particles or liquid droplets or a combination of solid particles and liquid droplets.

Advantageously, the modular smoking system further comprises: a first aerosol analysis module couplable to a first analysis port, the first analysis port being associated with a first smoking article port via a first aerosol-flow channel, and a second aerosol analysis module couplable to a second analysis port, the second analysis port being associated with a second smoking article port via a second aerosol-flow channel, in which an aerosol-flow-path between the first smoking article port and the first analysis module is of the same length as an aerosol-flow-path between the second smoking article port and the second analysis module.

The modular smoking system may further comprise a plurality of aerosol analysis modules, each of the plurality of aerosol analysis modules being couplable to an analysis port, an aerosol-flow-path between each of the plurality of aerosol analysis ports and a coupled analysis port being substantially identically dimensioned.

By providing identical flow path length to each smoking module, the results of an analysis carried out from different smoking article ports can be validly compared without the need for any adjustment of results.

Advantageously, the modular smoking system is capable of operating in either linear or rotary smoking mode, in which an aerosol-flow-path is of identical length when operated in both linear and rotary smoking modes. This provides the advantage that analysis results obtained from the different smoking modes may be validly compared. In this context, a "linear" mode is a mode in which aerosol is analysed per smoking article port, and a "rotary" mode is a mode in which aerosol is collected cumulatively for a plurality of smoking article ports.

The modular smoking system may comprise at least two different types of aerosol analysis module for carrying out at least two different types of aerosol analysis. Currently, several different types of analysis must be performed to provide a full characterisation and assessment of a smoking article. The provision of a modular system in which different analysis modules can be used, reduces the costs associated with the need for a plurality of smoking machines in terms of initial investment, maintenance and user training. The provision of a modular system in which different analysis modules can be used also provides flexibility to meet specific user requirements for different types of smoking article.

Several different types of analysis module can be used. The constituents of interest within the aerosol will determine the module or combination of modules needed. There are also different techniques and apparatus for measuring specific aerosol constituents, or the properties of an aerosol as a whole, that are known in the art. The following are examples of analysis modules that can be used alone or in combination. However, other analysis modules may be used as desired.

analysis module for manual or automatic total particulate matter (TPM) determination, with or without automatic filter extraction;
    analysis module for whole smoke analysis (e.g., a cold trap);
    an impinger to bubble aerosol through a liquid; and/or
    Puff-by-puff on-line analysis module for one or more specific constituents, such as carbon monoxide.

The inner surface of the carousel may be located within a first region that is sealed from the outer surface of the carousel such that secondary aerosol generated by the smoking of a smoking article while coupled to a smoking article port is retained within the first region. This may provide a preferable operating environment for some users. Furthermore, secondary aerosol retained within the first region may be transferred to a secondary aerosol analysis module to be analysed.

The carousel may comprise a first ring and a second ring, the first ring defining the inner surface of the carousel and having a plurality of channels extending radially through the first ring between the inner surface and an outer surface of the first ring, and the outer ring defining the outer surface of the carousel and having a plurality of channels extending radially through the second ring between an inner surface of the second ring and the outer surface, the plurality of channels defined through the first ring being capable of being disposed in overlapping relationship with the plurality of channels defined through the second ring to define the aerosol-flow channels.

Both the first ring and the second ring may be static such that each smoking article port located at the inner surface of the carousel is associated with a corresponding analysis port located at the outer surface of the carousel.

Alternatively, the first ring may be rotatable relative to the second ring such that each smoking article port located at the inner surface of the carousel may be associated with any of the plurality of analysis ports located at the outer surface of the carousel.

The modular smoking system may further comprise additional components, which may be known in the art, provided as interchangeable modules, in addition to the carousel and analysis modules. For example, the system may comprise one or more of the following: a transmission module, a magazine module, a product loader module, a product ignition module, a product ejector module, a waste collection module, a utility supply module, a side stream module, a configuration module, a database module, a data transfer module, an automation module, a GUI module, a machine safety module, a pick and place module, a device handling module, a pump module, and a dilution module. Each module is set up and calibrated for a range and set of application parameters. Once the desired modules are assembled, the smoking system may undergo integration testing, with all the parameters for each module defined and set before the integration testing (excluding the parameters defined by the configuration module if this module is used).

The modular smoking system may comprise suction means to draw aerosol through the analysis port and into the analysis module. The suction means may be provided as part of the analysis module or may be provided as a separate module. The suction means may be a gas syringe or pump.

In a second aspect, there is provided a method of analysing an aerosol generated by a smoking article comprising the steps of: locating a mouthpiece end of the smoking article in a smoking article port located on an inner surface of an annular carousel in a smoking machine, such that the smoking article extends radially inwards from the carousel, drawing an aerosol generated by the smoking article through a radially extending channel defined through the carousel and into a first analysis module located on an outer surface of the carousel, rotating the inner surface of the carousel relative to the outer surface of the carousel, and drawing an aerosol generated by the smoking article through a radially extending channel defined through the carousel and into a second analysis module located on the outer surface of the carousel, the second analysis module performing a different analysis to the first analysis module.

The method may be performed on an apparatus according to the first aspect.

In a third aspect, there is provided a method of simultaneously analysing aerosol generated by a plurality of smoking articles comprising the steps of locating a mouthpiece end of each of the plurality of smoking articles in one of a plurality of smoking article ports located on an inner surface of an annular carousel in a smoking machine, such that each of the plurality of smoking articles extends radially inwards from the carousel, and drawing an aerosol generated by each one of the plurality of smoking articles along an aerosol-flow-path and into one of a corresponding plurality of analysis modules located on an outer surface of the carousel, the aerosol-flow-path between each of the plurality of smoking articles and its corresponding analysis module being identically dimensioned.

The analysis modules may be identical to one another or different to one another.

It should be clear that features described in relation to one aspect might equally be applied to other aspects of the invention.

BRIEF DESCRIPTION OF THE DRAWINGS

Specific embodiments of the invention will now be described, by way of example only, with reference to the figures in which.

DETAILED DESCRIPTION

Figure 1:
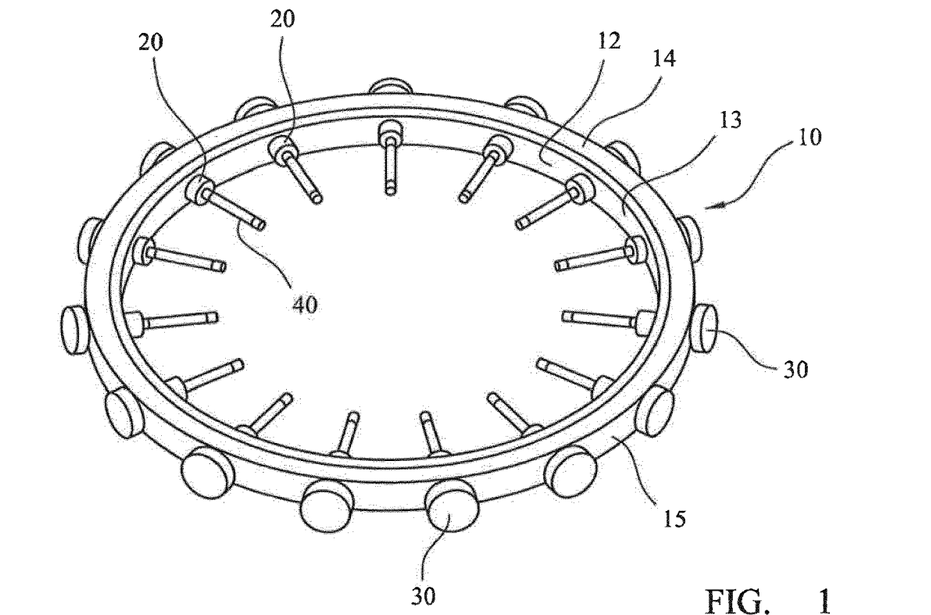
FIG. 1 is a schematic perspective illustration of a multi-port carousel module for a modular smoking system.

FIG. 1 illustrates a carousel module 10 for a modular smoking system. The carousel module 10 comprises two meshed, concentric, rings; an inner ring 12 and an outer ring 14. The inner ring defines an inner surface 13, and the outer ring defines an outer surface 15 that is radially spaced from the inner surface 13. A plurality of smoking article ports 20 is located at the inner surface 13. A plurality of analysis ports 30 is disposed at the outer surface 15. Although any number of analysis ports may be provided depending on the size of the carousel, between 8 and 24 ports has been found to be a good number. Each of the smoking article ports 20 is capable of receiving a smoking article 40 such that, when operated, mainstream smoke generated by the smoking article 40 is drawn into the smoking article port 20.

Figure 2:
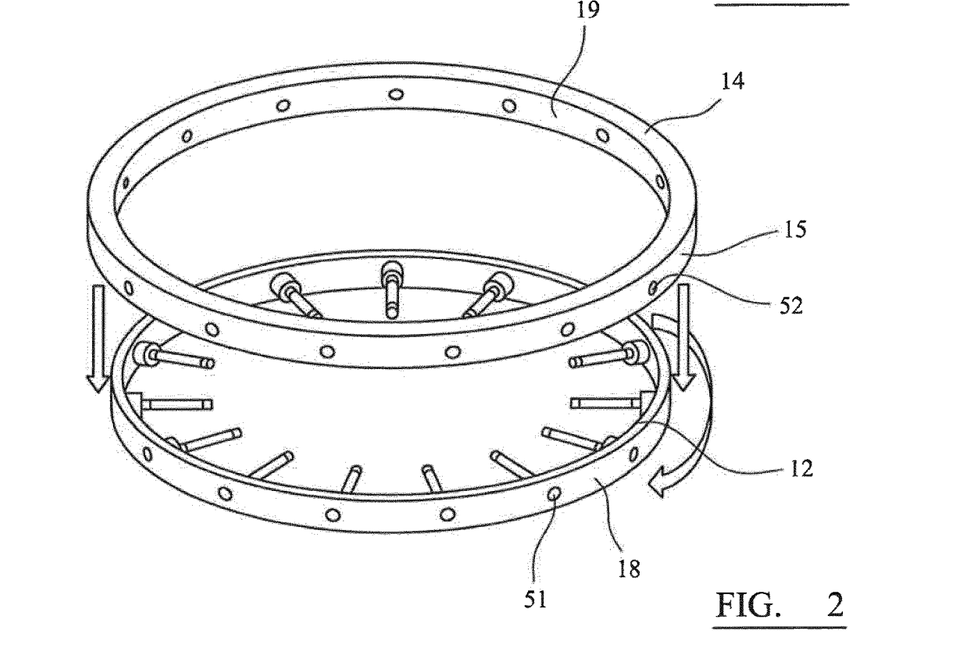
FIG. 2 is a schematic perspective illustration of the carousel module of FIG. 1 showing the two concentric rings forming part of the carousel module.
Figure 3:
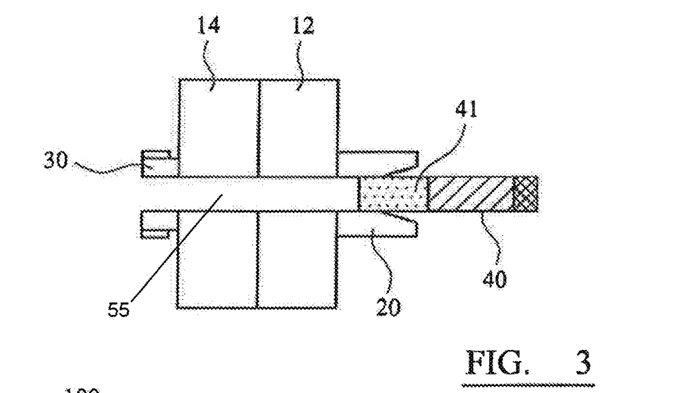
FIG. 3 is a cross-sectional illustration showing an aerosol-flow channel defined through a portion of the carousel module.

FIGS. 2 and 3 illustrate further details of the carousel module 10. In FIG. 2, the outer ring 14 is shown separated from the inner ring 12. Radially extending channels 51 extend through the inner ring 12 between the inner surface 13 and an outer surface of the inner ring 18. Likewise, radially extending channels 52 extend through the outer ring between an inner surface of the outer ring 19 and the outer surface 15. The outer surface of the inner ring 18 and the inner surface of the outer ring 19, when the carousel module is assembled, are arranged in sliding engagement such that the inner ring is rotatable relative to the outer ring. Radially extending channels defined through the inner ring 51 are positioned such that they may overlap with radially extending channels through the outer ring 52, thereby forming aerosol flow channels 55 that extend radially through both inner and outer rings of the carousel module 10. When fully assembled, the aerosol flow channels 55 extend radially through the carousel module 10 between a smoking article port 20 and an analysis port 30, such that aerosol generated by a smoking article 40 received within a smoking article port 20 can be drawn through an aerosol flow channel 55 and into an analysis module 100 coupled to an analysis port 30.

A cross-sectional illustration of the aerosol flow channel 55 is provided in FIG. 3. In this figure it can be seen that a smoking article port 20 is dimensioned to receive a mouthpiece end 41 of a smoking article 40. The smoking article port 20 may comprise a labyrinth seal for sealing around the smoking article 40. Aerosol generated by the smoking article 40 may be drawn through the aerosol flow channel 55 defined through the carousel module and pass into an analysis module, or any other module, attached or coupled to an analysis port 30.

A smoking article may be a conventional cigarette, or other aerosol generating means such as a heated cigarette.

An advantage of the modular smoking system as described herein is the ability to arrange more than one aerosol analysis module simultaneously within the system such that any aerosol flow path between a smoking article 40 and an analysis module 100, 110 is of minimal length and also of substantially identical dimensions to other aerosol flow paths.

It may be desirable to position an aerosol analysis module as closely as possible to a smoking article in a smoking machine in order to receive the aerosol within a short distance after it passes out of the smoking article. An aerosol, such as smoke, that is drawn from a smoking article may be altered if it passes down a long or convoluted aerosol flow path. Therefore, it is difficult to produce accurate results using analysis machines located at a distance from an aerosol generating device such as a smoking article. In standard smoking machines, smoking article ports are arranged on an external surface of a carousel and ports for transferring aerosol to one or more analysis units are located radially inside the smoking article ports. Thus, there is no room provided for analysis units and any aerosol generated by the smoking articles needs to be transferred to respective analysis units.

Figure 4:
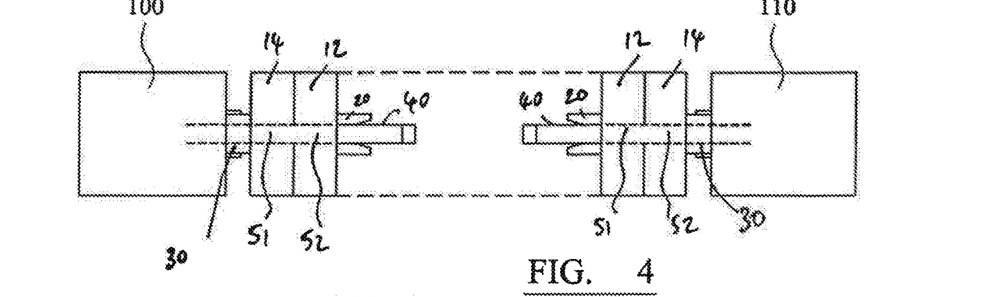
FIG. 4 is a cross-sectional illustration of the carousel of FIG. 1 illustrating two analysis models coupled to the carousel module.

By arranging more than one analysis module 100, 110 around the periphery of a carousel module it is possible to ensure that any aerosol flow path between a smoking article port and an analysis module 100, 110 is identically dimensioned. FIG. 4 shows a carousel module as described above when coupled to a first analysis module 100 and a second analysis module 110. The first and second analysis modules analyse different aspects of the aerosol generated by the smoking articles 40. The arrangement of the respective analysis modules in a position radially outside of the carousel module 10 allows the aerosol flow path to each analysis module to be substantially identically dimensioned. Furthermore, there is ample space to access each analysis module during both assembly and disassembly of the system and during operation of the system.

The inner ring 12 comprises indexing means allowing it to be rotated relative to the outer ring 14, which is static. Channels 51 defined through the inner ring 12 may be brought sequentially into alignment with channels 52 defined through the static outer ring 14. In this way, any single smoking article 40 may be analysed by a plurality of analysis modules, each analysis module coupled to a different analysis port 30. Also a plurality of smoking articles may be analysed by a single analysis module, corresponding to a rotational mode of operation.

Figure 5:
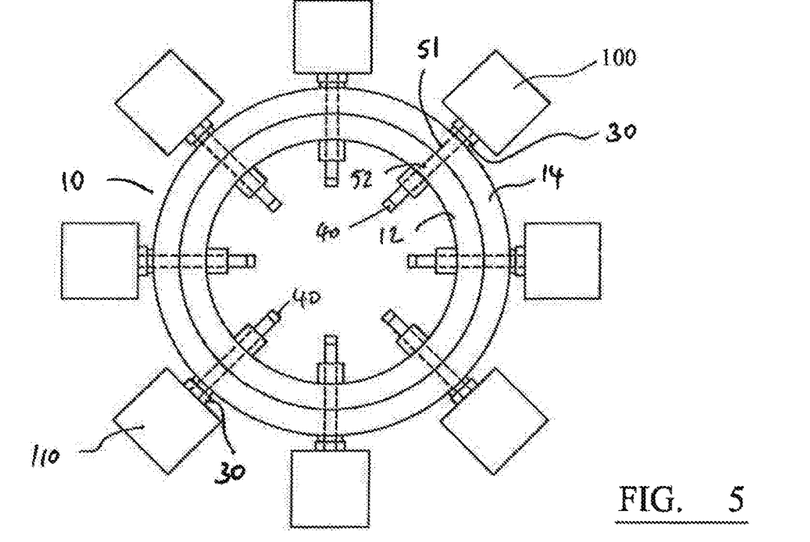
FIG. 5 is a schematic plan view of a portion of a modular smoking machine showing a carousel module coupled to a plurality of analysis modules.

FIG. 5 provides a plan view of a carousel module coupled to a plurality of analysis modules. In the embodiment shown in FIG. 5, each of a plurality of smoking articles may be analysed by an analysis module simultaneously. The analysis modules may each be performing the same type of analysis, or each analysis module may analyse a different aspect of the aerosol generated by the smoking article. The system may operation a linear mode in which each analysis module is configured to analyse individual smoking articles, or a rotational mode, in which each analysis module is configured to analyse aerosol collected from a plurality of smoking articles, sequentially rotated into alignment with the analysis module.

Any suitable rotation drive may be provided (not shown), such as a stepper motor or servo motor, and any suitable control and gearing mechanism may be used to ensure correct alignment of the inner and outer rings 12, 14.

Smoking articles in the form of conventional cigarettes, or heated cigarettes with an integral combustible heat source, may conveniently be self-supporting when inserted into the smoking article ports. Thus, such smoking articles are entirely supported when their respective mouth-ends are received in smoking article ports. Other types of smoking article, for example electrically heated smoking articles or electrically operated aerosol-generating articles, may require additional support means, which may be provided by a support module.

Figure 6:
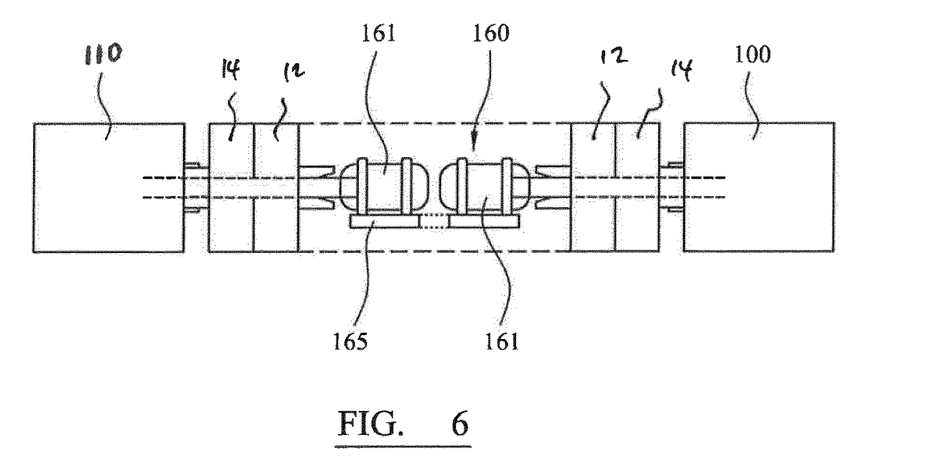
FIG. 6 is a cross-sectional illustration of a portion of a modular smoking machine illustrating a carousel module and a support module for supporting electrically operated smoking devices.

FIG. 6 illustrates an embodiment of a modular smoking system further comprising a support module 160 having an annular support 165 for supporting smoking devices 161 in a position such that the mouth-end of the devices may be received into smoking article ports of a carousel module as described above.

Figure 7:
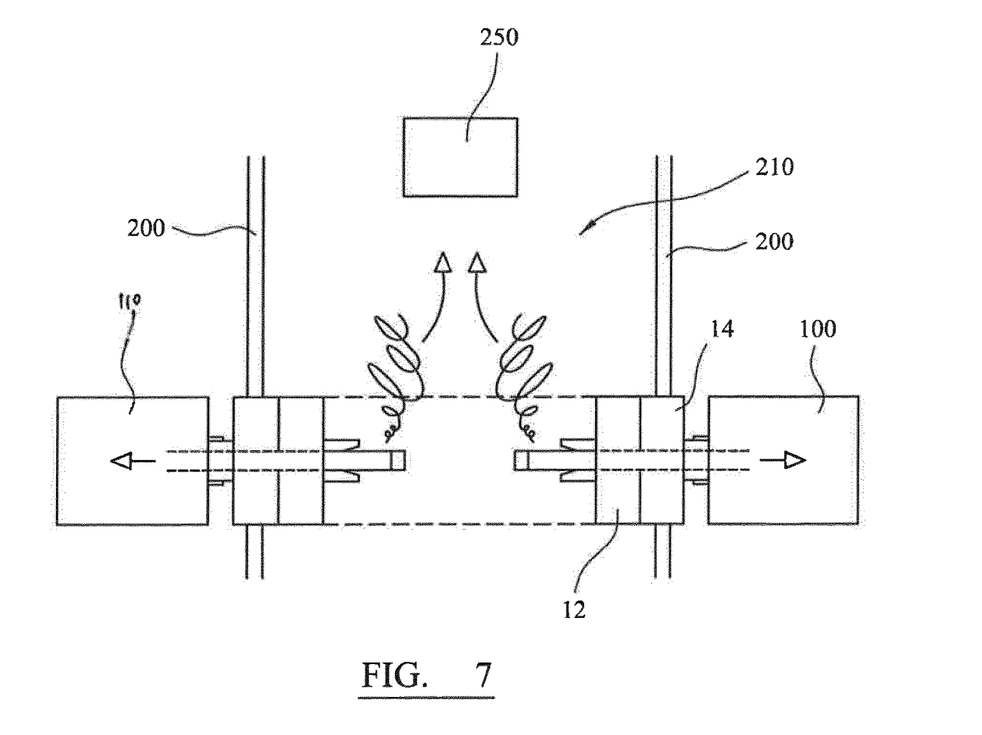
FIG. 7 is a cross-sectional illustration of a portion of a modular smoking system showing a carousel module having a sealed inner region for the collection of secondary smoke during operation of the modular smoking system.

While analysis of mainstream smoke generators by a smoking article has been described above, it may be desirable also to analyse secondary or sidestream smoke evolved from a smoking article during a smoking process. In a conventional smoking machine it is difficult to accurately retrieve sidestream smoke evolved from a smoking article smoked in the smoking machine. A potentially advantageous embodiment of the invention, as illustrated in FIG. 7, may allow sidestream smoke to be efficiently recovered.

Walls 200 extending from a static outer ring 14 of a carousel module enclose a sealed region 210 encompassing a rotatable inner ring 12 of the carousel module. Smoking articles received in the carousel module extend radially inwards from the inner ring 12 and are thus contained within the sealed region 210 during operation of the modular smoking machine. By sealing this inner region, it is possible to extract any sidestream smoke generated by the smoking articles during operation of the smoking machine using a sidestream module, and to analyse any such sidestream smoke that is extracted, for example in a further analysis module 250. Thus, the modular smoking system as described herein may be capable of analysing simultaneously both mainstream smoke and sidestream smoke generated by a plurality of smoking articles. Sealing the inner region from the operator may also provide a preferable operating environment for some users.

Figure 8:
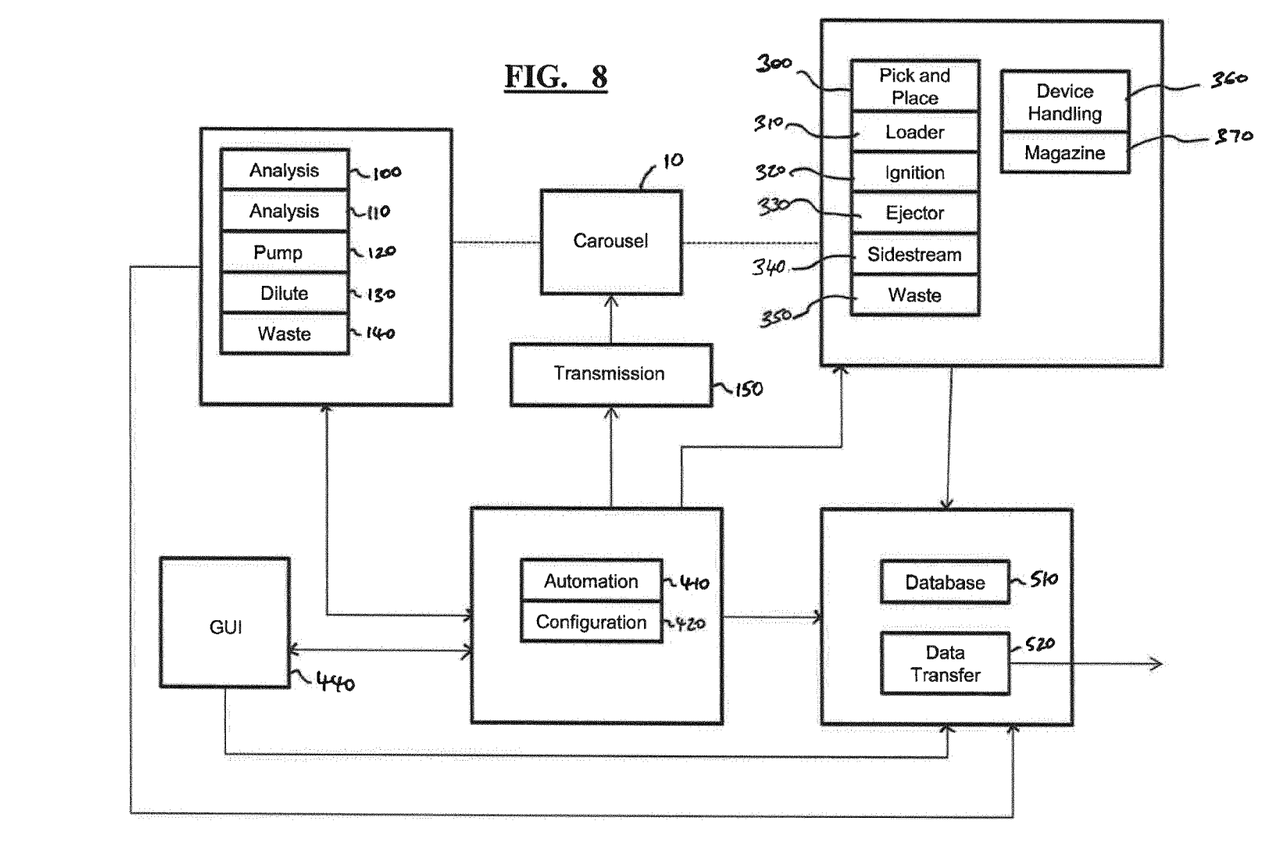
FIG. 8 is a schematic illustration of a modular smoking system including a carousel module.

Further components of the smoking system may be provided to make the operation of the system fully automated. These components may be provided as further modules. FIG. 8 is a schematic diagram showing possible further modules, which may be used in various combinations.

The carousel 10 is rotated by the transmission module 150. The transmission module may be a stepper motor or servo motor that rotates the inner ring 12. The transmission module is controlled by the automation module 410. The automation module includes a programmable logic controller or microprocessor running software. Another control module is the configuration module, which comprises software running on a microprocessor to carry out automatic configuration of the system.

The analysis modules 100, 110 are shown together with other modules on the outer side of the carousel. The pump module 120 is used to draw air through the smoking article. The pump module may comprise a single piston or may comprise a double piston to achieve continuous smoking. The pump module is controlled by the automation module to provide a desired puff profile. The dilute module 130 is used to dilute a continuous flow of aerosol to achieve a target concentration. The dilution may be achieved in a single step or in several steps. The waste module 140 collects waste analysis products.

On the inner side of the carousel, there are a plurality of further modules that may be used. These modules are also controlled by the automation module 410. The ignition module 320 lights the smoking article according to a lighting protocol. The lighting may be performed when the smoking article is on the carousel or may be performed before the smoking article is loaded on to the carousel. Depending on the type of smoking article, different lighting methods may be used. The loader module 310 loads the smoking article on to the carousel. The smoking article may be a cigarette, or an electronic smoking device, or a smoking device with a cigarette. The pick and place module 300 transports the smoking article from a product handling or ignition module to the loader module 310. For reusable smoking articles, the pick and place module 300 may also move the smoking article back to a device-handling module after use. The device-handling module 360 handles smoking devices away from the carousel and may perform operations such as battery charging, device verification, and re-filling. The ejector module 330 verifies if ejection conditions are met and then ejects the smoking article. If a device-handling module is included in the system, then the ejector module may eject cigarettes from the devices. Otherwise, the ejector unit may eject smoking articles directly from the smoking ports. The sidestream module 340 controls airflow around the smoking article and evacuates the sidestream smoke. The magazine module 370 contains a limited number of smoking articles for one smokerun. A smokerun can be the smoking of one smoking article up to a smokerun of several hours per day to enable acute, chronic or sub-chronic exposure of cells or animals. The magazine module supports this by providing a capacity in line with the duration of the smoke run. The magazine module releases smoking articles on demand of the system.

The waste module 350 collects ashes from the smoking articles and collects used smoking article butts into a waste container.

A graphical user interface (GUI) module 440 is provided to allow a user to control and configure the system, and view data. The GUI module may also require the entering of user access passwords.

Data modules are provided to record and transfer smoking machine data. The database module 510 captures data obtained from the analysis modules and from the operation of the other modules. A data transfer module 520 may be provided to automatically transfer the captured data, or portions of the captured data, to an external database.

A utility supply module may also be included. A utility supply module comprises a central connection for utility supplies with a distribution grid and regulates the utility to be supplied. For example, for compressed air it is connection tubing with a quick connector to connect to the grid, a pressure regulator to set and maintain accurately the pressure and a distribution line with a plurality of connection points. Each module that needs compressed air has tubing with a quick connector that is connected to the supply unit in case the module is installed on the system.

A safety module may also be used. The safety module contains a certified safety relay and, for example, light barriers or magnetic contacts, to ensure that an operator will not be exposed to hazards. The safety module ensures machine stop before the machine dynamics or power source can affect the operator. The safety module may, for example, include SIRIUS 3SK1 Safety Relays available from Siemens AG, Industry Automation Control Components and Systems Engineering, Postfach 23 55, 90713 Fürth, GERMANY.

The exemplary embodiments described above illustrate but are not limiting. In view of the above-discussed exemplary embodiments, other embodiments consistent with the above exemplary embodiments will now be apparent to one of ordinary skill in the art.

The invention claimed is:

1. A modular smoking system, comprising-,
   a carousel module comprising a substantially annular carousel, a plurality of smoking article ports configured to receive smoking articles, and a plurality of analysis ports,
      the substantially annular carousel comprising at least one ring having an inner surface and an outer surface radially spaced from the inner surface, through which a plurality of identically-dimensioned aerosol-flow channels are defined through the substantially annular carousel, and
      each aerosol-flow channel of the plurality of aerosol-flow channels extending radially through the at least one ring of the substantially annular carousel between a smoking article port of the plurality of smoking article ports located at the inner surface of the at least one ring and an analysis port of the plurality of analysis ports located at the outer surface of the at least one ring; and
   at least one aerosol analysis module, located radially outwards from the outer surface of the at least one ring and configured to couple to the analysis port, configured to analyze an aerosol generated by a smoking article coupled to the smoking article port,
   wherein the inner surface of the at least one ring is configured to rotate relative to the outer surface of the at least one ring.

2. The modular smoking system according to claim 1, the at least one aerosol analysis module further comprising:
   a first aerosol analysis module configured to couple to a first analysis port of the plurality of analysis ports, the first analysis port being associated with a first smoking article port of the plurality of smoking article ports via a first aerosol-flow channel of the plurality of aerosol-flow channels; and
   a second aerosol analysis module configured to couple to a second analysis port of the plurality of analysis ports, the second analysis port being associated with a second smoking article port of the plurality of smoking article ports via a second aerosol-flow channel of the plurality of aerosol-flow channels,
   in which an aerosol-flow-path between the first smoking article port and the first aerosol analysis module has a same length as another aerosol-flow-path between the second smoking article port and the second aerosol analysis module.

3. The modular smoking system according to claim 1, the at least one aerosol analysis module further comprising a plurality of aerosol analysis modules, each of the plurality of aerosol analysis modules being configured to couple to a corresponding analysis port of the plurality of analysis ports, aerosol-flow-paths between said each of the plurality of aerosol analysis modules and a coupled corresponding analysis port being substantially identically dimensioned.

4. The modular smoking system according to claim 1,
   wherein the system is configured to operate in either a linear smoking mode or a rotary smoking mode, and
   wherein an aerosol-flow-path between the smoking article port of the plurality of smoking article ports and the analysis port of the plurality of analysis ports has an identical length when operated in a linear smoking mode as when operated in a rotary smoking mode.

5. The modular smoking system according to claim 1, comprising at least two different types of aerosol analysis modules configured to carry out at least two different types of aerosol analysis.

6. The modular smoking system according to claim 1, in which the inner surface of the substantially annular carousel is located within a first region that is sealed from the outer surface of the substantially annular carousel such that a secondary aerosol generated by smoking of the smoking article while coupled to the smoking article port of the plurality of smoking article ports is retained within the first region.

7. The modular smoking system according to claim 6, the system being configured to transfer the secondary aerosol retained within the first region to a secondary aerosol analysis module to be analysed.

8. The modular smoking system according to claim 1, in which the at least one ring of the substantially annular carousel comprises a first ring and a second ring,
   the first ring defining the inner surface of the substantially annular carousel and having a plurality of channels extending radially through the first ring between the inner surface and an outer surface of the first ring, and
   the second ring defining the outer surface of the substantially annular carousel and having another plurality of channels extending radially through the second ring between an inner surface of the second ring and the outer surface,
   the plurality of channels defined through the first ring are configured to be disposed in an overlapping relationship with the another plurality of channels defined through the second ring to define the aerosol-flow channels.

9. The modular smoking system according to claim 8, in which both the first ring and the second ring are configured such that each smoking article port of the plurality of smoking article ports located at the inner surface of the substantially annular carousel is associated with a corresponding analysis port of the plurality of analysis ports located at the outer surface of the substantially annular carousel.

10. The modular smoking system according to claim 8, in which the first ring is configured to be rotatable relative to the second ring such that each smoking article port of the plurality of smoking article ports located at the inner surface of the substantially annular carousel is configured to be associated with any of the plurality of analysis ports located at the outer surface of the substantially annular carousel.

11. The modular smoking system according to claim 1, further comprising at least one module selected from the list comprising: a transmission module, a magazine module, a product loader module, a product ignition module, a product ejector module, a waste collection module, a utility supply module, a side stream module, a configuration module, a database module, a data transfer module, an automation module, a GUI module, a machine safety module, a pick and place module, a device handling module, a pump module, and a dilution module.

12. A method of analysing an aerosol generated by a smoking article, comprising:
  placing a mouthpiece end of the smoking article in a smoking article port located on an inner surface of at least one ring of an annular carousel in a modular smoking system having a plurality of smoking article ports and a plurality of analysis ports, such that the smoking article extends radially inwards from the inner surface of the at least one ring;
  drawing the aerosol generated by the smoking article through a radially extending channel defined through the at least one ring of the annular carousel and into a first analysis module located on an outer surface of the at least one ring;
  rotating the inner surface of the at least one ring relative to the outer surface of the at least one ring; and
  drawing the aerosol generated by the smoking article through another radially extending channel defined through the at least one ring and into a second analysis module located on the outer surface of the at least one ring, the second analysis module performing a different analysis than the first analysis module.

13. The method according to claim 12,
  wherein the method is performed on the modular smoking system in which the at least one ring of the annular carousel comprises a first ring and a second ring, the first ring being rotatable relative to the second ring such that each smoking article port of the plurality of smoking article ports located at the inner surface of the at least one ring is configured to be associated with the first analysis module or the second analysis module,
  wherein the outer surface of the at least one ring is radially spaced from the inner surface,
  wherein the radially extending channel extends between a smoking article port of the plurality of smoking article ports and an analysis port of the plurality of analysis ports located at the outer surface, and the first analysis module is coupled to the analysis port, and
  wherein the another radially extending channel extends between another smoking article port of the plurality of smoking article ports and another analysis port of the plurality of analysis ports located at the outer surface, and the second analysis module is coupled to the another analysis port.

14. A method of simultaneously analysing aerosol generated by a plurality of smoking articles, comprising:
  placing a mouthpiece end of each smoking article of the plurality of smoking articles in a corresponding smoking article port of a plurality of smoking article ports located on an inner surface of at least one ring of an annular carousel in a smoking machine, such that each of the plurality of smoking articles extends radially inwards from the at least one ring; and
  drawing the aerosol generated by each smoking article of the plurality of smoking articles along an aerosol-flow-path and into a corresponding analysis module of a plurality of analysis modules located on an outer surface of the at least one ring, aerosol-flow-paths between said each of the plurality of smoking articles and the corresponding analysis module being identically dimensioned,
  wherein the inner surface of the at least one ring is configured to rotate relative to the outer surface of the at least one ring.

* * * * *